United States Patent [19]
Mougne

[11] Patent Number: 5,067,345
[45] Date of Patent: * Nov. 26, 1991

[54] METHOD AND APPARATUS FOR MEASURING AND CALCULATING BULK WATER IN CRUDE OIL OR BULK WATER IN STEAM

[76] Inventor: Marcel L. Mougne, 1107 Briarpark Dr., Houston, Tex. 77042

[*] Notice: The portion of the term of this patent subsequent to Apr. 17, 2007 has been disclaimed.

[21] Appl. No.: 509,896

[22] Filed: Apr. 16, 1990

Related U.S. Application Data

[63] Continuation-in-part of Ser. No. 215,058, Jul. 5, 1988, Pat. No. 4,916,940.

[51] Int. Cl.$^5$ ............... G01N 27/22; G01N 33/22
[52] U.S. Cl. ............................ 73/61.10 R; 324/664
[58] Field of Search ............... 73/61.1 R, 29.1, 25.04; 324/664

[56] References Cited
U.S. PATENT DOCUMENTS

| | | | |
|---|---|---|---|
| 4,769,593 | 9/1988 | Reed et al. | 73/29.01 X |
| 4,849,988 | 7/1989 | Chien | 73/29.01 X |
| 4,916,940 | 4/1990 | Mougne | 73/61.1 R |

Primary Examiner—Hezron E. Williams
Assistant Examiner—Joseph W. Roskos
Attorney, Agent, or Firm—J. David Cabello

[57] ABSTRACT

The present invention discloses an apparatus and method for continuous measurement of water volume in oil or steam which overcomes many of the shortcomings. In the present invention may shortcomings encountered in the prior art devices are overcome by placing a dielectric capacity probe inside the main pipeline, to measure the average dielectric constant (E) of the flowing mixture. This 'in situ' sampling, will account for the entire cross-sectional area of the pipe or duct and its contents. The 'in-situ' probe will have a high intrinsic capacitance approaching that of air, which has a dielectric constant equal to "1". The probe placed within the pipeline shall offer a minimal impedance to flow of the crude oil or steam and the oil's normal impurities and sediments. The probe will automatically self-calibrate, 'in-line', at selected time intervals and shall be fully automated for the overall routine operation. Additionally it is an object of the present invention to continuously correct the measured capacitance as the temperature fluctuates throughout delivery.

22 Claims, 6 Drawing Sheets

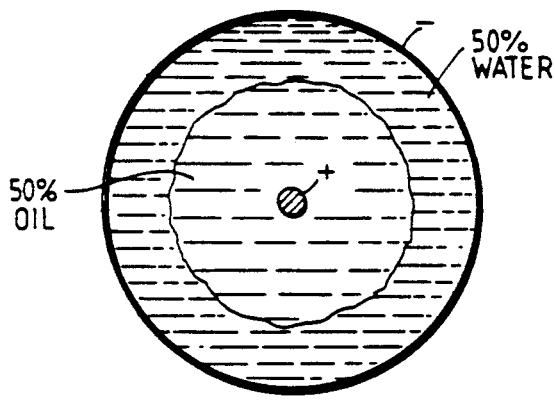
FIG.1A
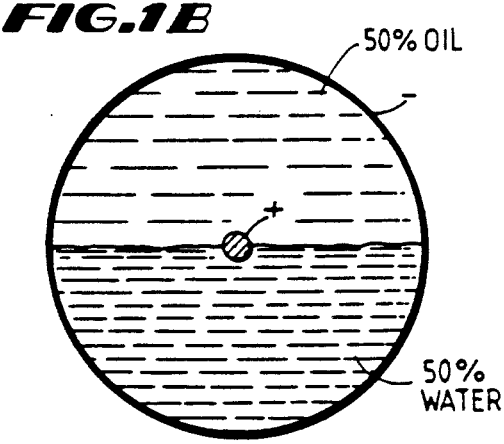
FIG.1B
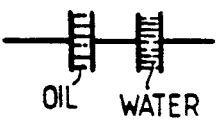
FIG.1AA (EQUIVALENT = 2 CAPACITORS IN SERIES.)
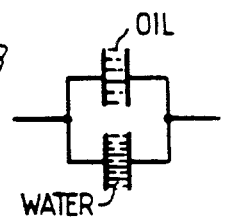
FIG.1BB (EQUIVALENT = 2 CAPACITORS IN PARALLEL.)
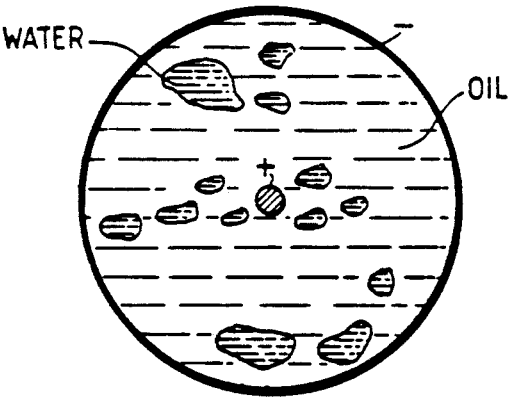
FIG.1C
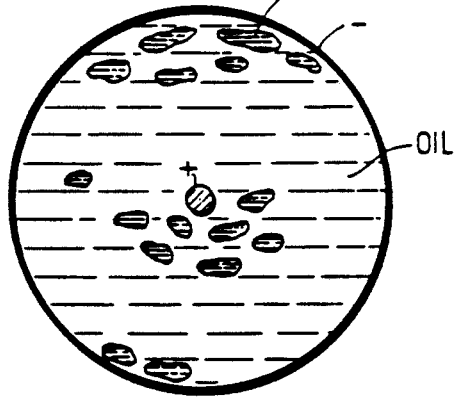
FIG.1D
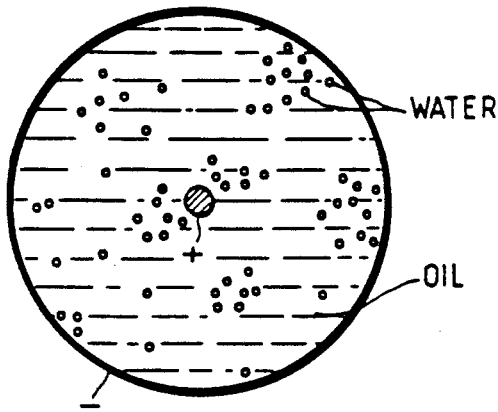
FIG.1E (WATER DROPLETS DISPERSED IN OIL)

(WATER SEGREGATED AT FLOOR OF DUCT)

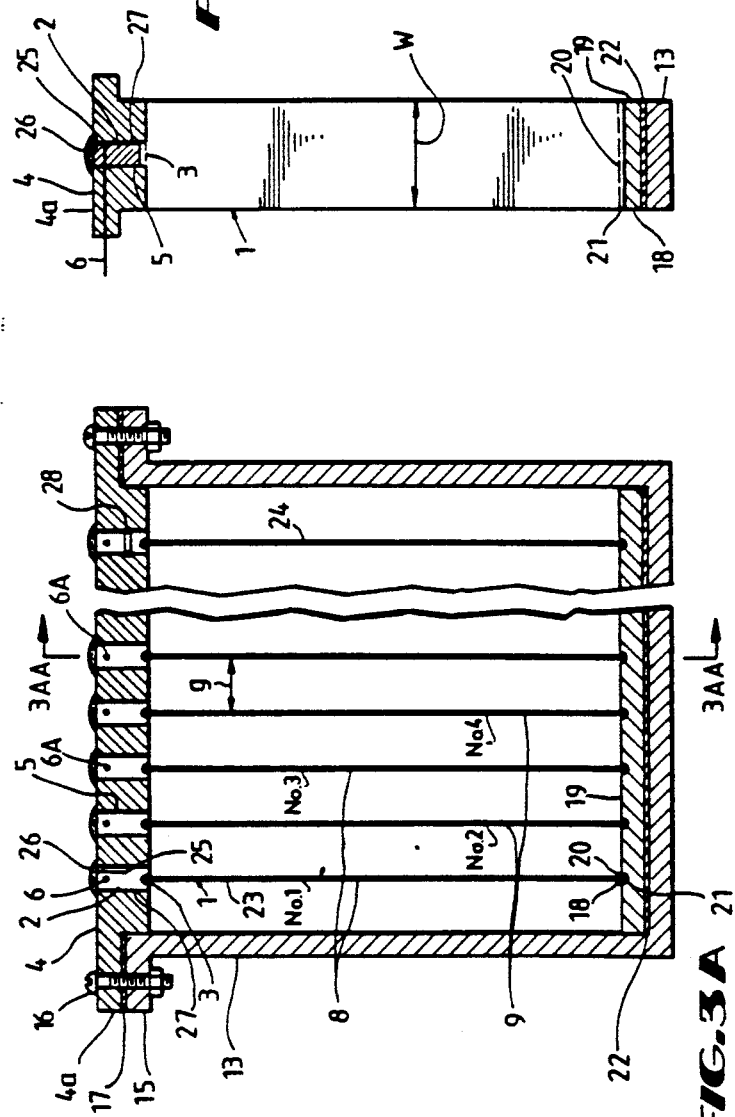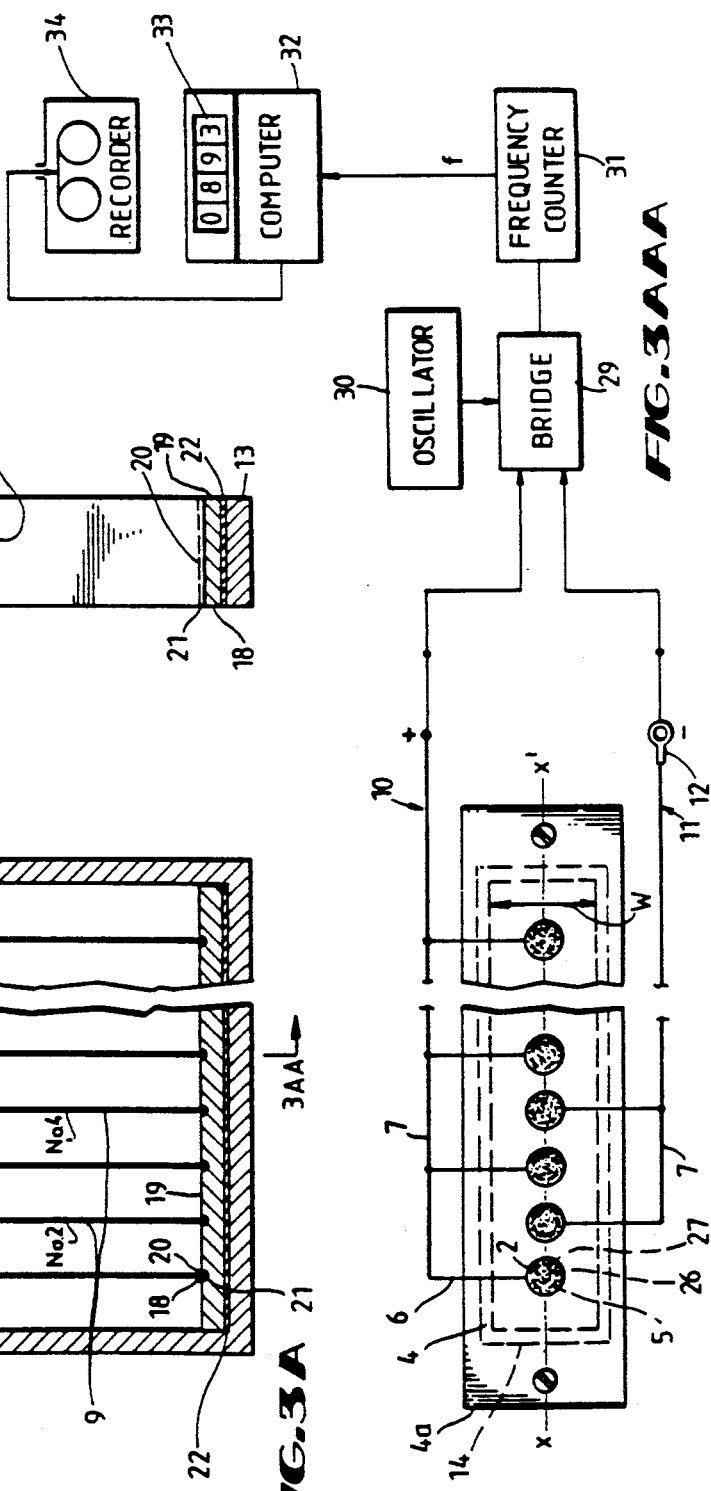

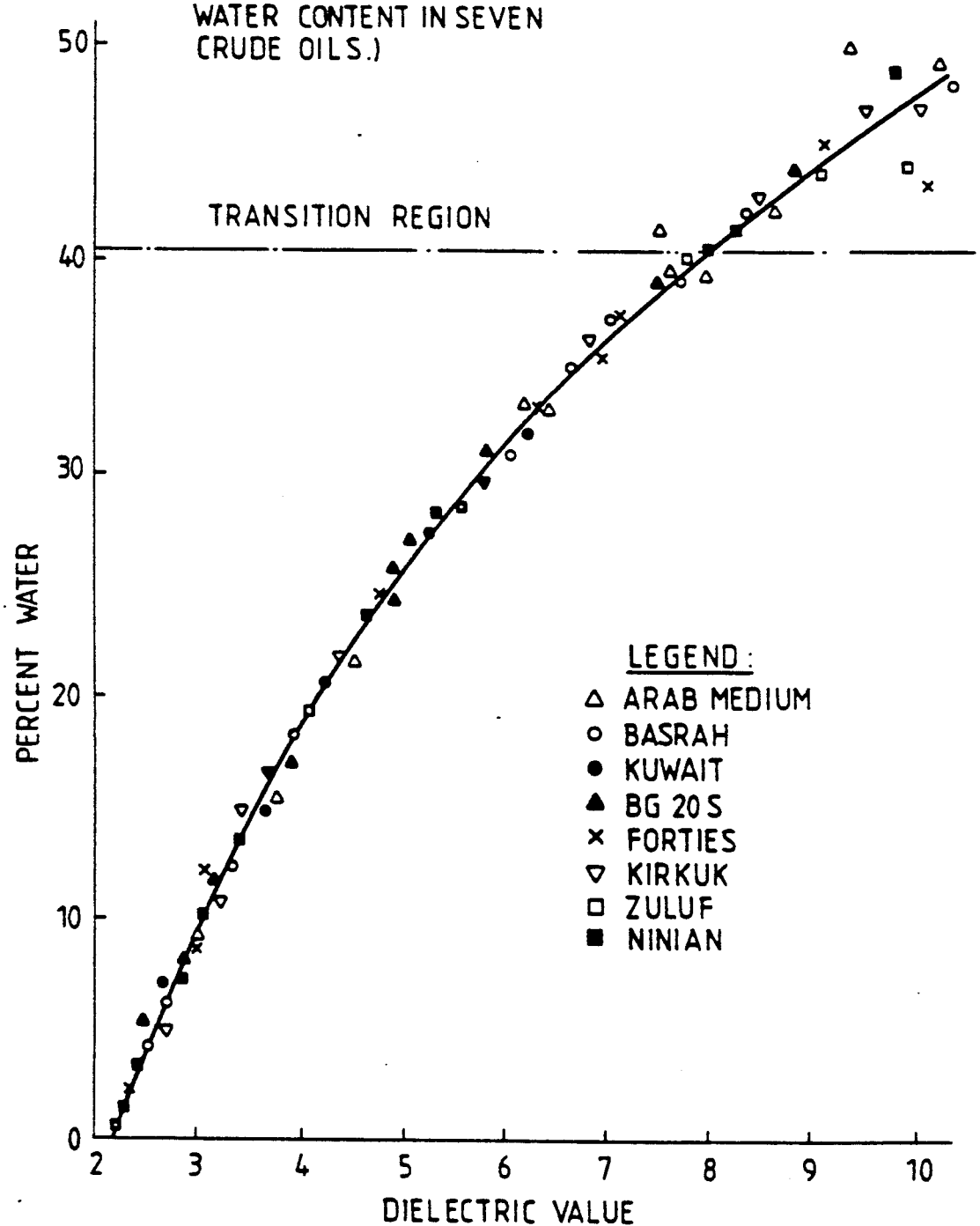

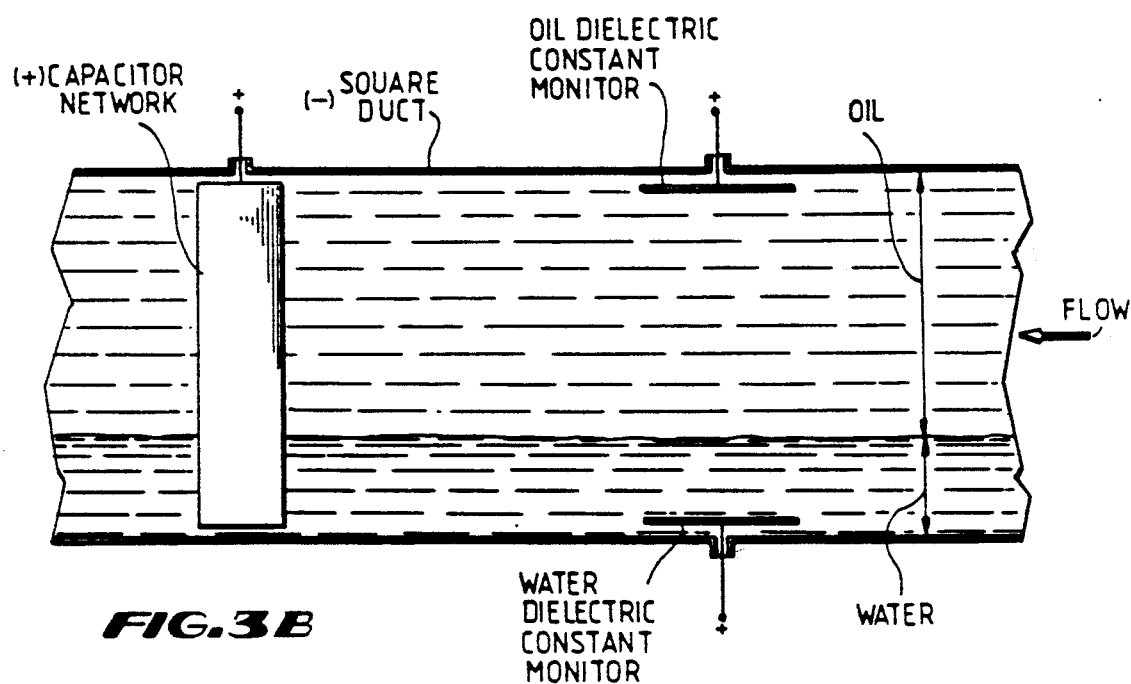
FIG.3B
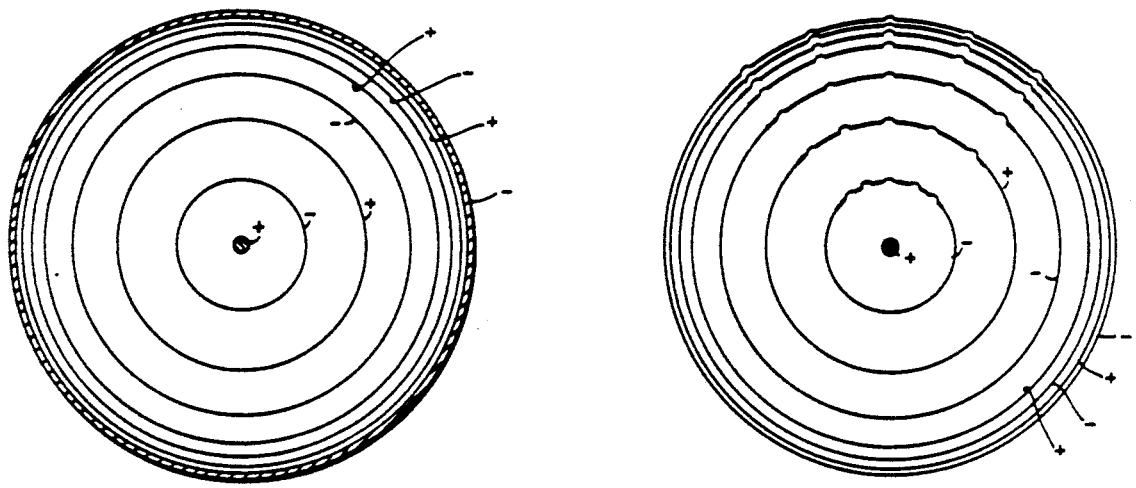
FIG.7A  FIG.7B

METHOD AND APPARATUS FOR MEASURING AND CALCULATING BULK WATER IN CRUDE OIL OR BULK WATER IN STEAM

RELATED APPLICATIONS

This application is a continuation-in-part of U.S. patent application Ser. No. 07/215,058 filed July 5, 1988, now U.S. Pat. No. 4,916,940.

BACKGROUND OF THE INVENTION

This invention relates to a method and apparatus for measuring the dielectric constant of a non-homogeneous mixture to determine the concentration of various components in this mixture. Specifically the invention relates an improved method and apparatus for measuring the dielectric constant of crude oil as it is transferred in order to determine the percentage of water contained in the crude, or of water in the liquid phase in a steam gaseous phase.

BRIEF DESCRIPTION OF THE PRIOR ART

Dielectric constant (E) measurements performed for the determination of 'fractional volume' composition of two immersible fluids, have been utilized for many years. Such dielectric methods are particularly useful when it is necessary to distinguish different volumes of mixtures of highly varied dielectric constants (E's). Two practical applications of the method are:

1) Determining the proportion of water (W) to oil (O) 'ratio' (W/O+W) in an oil pipeline or oil tank; since, the oil always contains minute to large quantities of water. The latter, being an amount of impurity of no commercial value, and which, should be accurately deducted from the total 'bulk volume' of delivered, purchased oil.

In a similar manner water volumes in steam can be evaluated to control steam quality during enhanced recovery operations by steam injection into heavy oil bearing strata.

2) At the well head, both water and oil are simultaneously produced. Probes, designated as "water cut" by design, using dielectric measurements, are run 'downhole' (in situ) into the flowing well to continuously monitor, the ratio (W/O+W).

The key unit which provides such (W/O+W) ratio determinations is the 'cylindrical capacitor'. The device has two electrodes which automatically measure the capacitance (Cd), and therefore, the dielectric constant (E) of the ratio (W/O+W) in the mixture, via two electrodes, against the 'standard' E of the particular air capacitor. For example, the dielectric constant (E) of water (80 to 200-depending directly on the salinity of the water) is significantly higher than the dielectric constant (E) of crude oil (2 to 3 depending on chemical composition). Fluctuations in the ratio (W/O+W) vary directly with the dielectric constant (E). The properties and specific dielectric constants (E's) of common and natural substances are available in most elementary physical tables.

However, the above method of determining the ratio (W/O+W) is accurate only if the tested mixture is homogeneous. Ideally, a homogeneous mixture contains uniformly dispersed, identical, macroscopic aggregates, of the chemically joined water and oil. These aggregates are considered, in theory, of the same fractional composition of ratio W/O+W as the surrounding mixture.

Experience reveals that such homogeneity, in mixtures, does not always exist. For example, in the first phase of discharging oil from a tanker at the oil terminal, water is the major fluid pumped out of the ship and into the discharge pipe inlet. This occurs, because the intake pipe is positioned on the floor of the ship's tank, where the water has settled during transport at sea. The pumping of the crude/water mixture continues until the amount of water becomes less than 1% of the flowing volume; thereafter the continuous discharge process enters the relatively longer duration second phase of pumping of the more undiluted (less water content), and commercially valuable crude oil. It is during this second phase of the discharging of oil, where the degree of homogeneity of the dispersed water-oil aggregates becomes rather speculative; and errors of $C_d$ measurements and the concomitant evaluation of oil volumes raise serious questions, in regards to accuracy.

A simple hypothetical model will serve to illustrate how the errors of volume analysis occur because of the erratic dispersion of water-oil aggregates.

According to designs presently used in the industry, the positive electrode of a cylindrical capacitor is a metal rod which is inserted along the longitudinal axis of an in-line pipe; the pipe, the pipeline itself becomes the negative electrode of the capacitor. Four possible considerations regarding identical volumes of water-in-oil are shown in FIGS. 1A,1B,1C,1D and 1E. FIG. 1A illustrates the electric equivalent of two capacitors connected in series due to the theoretical segregation of the oil and water. FIG. 1B illustrates the electric equivalent of two capacitors connected in parallel due to the theoretical segregation of the oil and water. The terms, in series and in parallel are conventional expressions of basic electricity. FIGS. 1C, 1D and 1E represent three additional potential mixtures of water in oil which would result in distinct combinations of capacitors connected in a number of in series and in parallel configurations. It follows, that different spatial distributions of the oil-water particles under identical quantities of volumes of oil in water, would yield different dielectric constants ($C_d$'s) and hence, different calculated volumes of fluid.

The prevailing system for measuring the dielectric constant ($C_d$) during the above mentioned second phase of the discharge process, is represented in FIG. 1E. The inherent shortcoming of this measurement system is due to the random heterogeneous dispersion of the minuscule water droplets across the cross-sectional area of pipe, where the electrodes are placed. In this imprecise condition the measurement of fractional volumes of water in oil, is far less than ideal; and still, the precision of this measurement is of utmost importance in everyday commercial transactions.

In recognition of the need for precise, consistent, reliable and exacting measurement systems, apparatus and methods have been devised to overcome the apparent problems of determining, precisely, the fractional volumes of water in oil.

Present methods of water in oil determinations use 'intermittent' sampling. Their complex approach is to:

1) Collect samples (via an in line tap), of the oil and water mixture from within the pipe, in sections of the line where fluid homogeneity is likely to exist, i.e. areas of turbulence, or eddies, created by bends or elbows in the pipe system.

2) Collect such samples at regular intervals of time.

3) Divert the sample to a conventional capacitor cell, and measure the capacitance ($C_d$) of the mixture.

4) Remove the water from the mixture by means of a centrifuge.

5) Again measure, in the capacitor cell, the capacitance ($C_d$) of the water-free oil.

6) Compare the values derived from steps 3) and 5) to determine the water volume in the mixture.

Several weaknesses of this technique are however inherent and must be examined.

A) It is imperative that the homogeneity of the sampled mixture directly reflect that of the source fluid mixture. Since this condition does not exist, an unknown factor exists in these methods, as to how perfectly the homogeneity of the sample matches that of the sampled fluid.

B) It follows, that a continuous monitoring of the fluid would give more accurate dielectric constant (E) measurements, viz-a-viz intermittent sampling; since, particulate dispersion configurations of the source mixture, will very likely change, between samplings.

C) Additionally these methods have no way of accounting for variations in temperature of the fluids. These temperature variations create an added complexity which must be accounted for.

A much more accurate method has been developed by Shell Oil Company. The accuracy of the water in oil evaluation is highly improved by conducting a continuous sampling of the pipe flow, rather than intermittently sampling the oil as previously described. Another method of determining the dielectric constant (E) in oil-water mixtures was developed by 'Endress and Hauser' in a joint effort with British Petroleum. That method is described as follows:

1) A small diameter by-pass pipe loop is diverted from the main pumping pipe. The loop contains a coaxial lead, which serves as the positive electrode of the cylindrical capacitor. The loop, itself, is the negative electrode of the capacitor.

2) Measurement of dielectric constant (E) is taken directly from the by-pass loop.

The 'Endress' system has an advantage in improved accuracy in that

A) Sampling is continuous, (as opposed to intermittent).

B) A greater degree of homogeneity of the sample is achieved, because the smaller diameter by-pass creates increased flow velocity (Venturi's effect) with a consequent increase in turbulence and shear forces (mixing) of the fluid.

C) The constricted by-pass, reduces the space between the capacitor's electrodes. Since interelectrode distance is inversely proportional to capacitance, i.e. the shorter the space the greater the capacitance, a greater accuracy of dielectric constant (E) measurement is possible. However, temperature fluctuations, hence, mathematical corrections, are necessary for an accurate determination of the dielectric constant (E).

Both the 'Shell' and 'Endress' methods of measuring dielectric constant (E) fail to account for the variations of the dielectric constant which are due to the assumption that the sample (drawn for the test) is a representative sample of the fluid volume flowing thru the pipe. Measurement systems which assume that the sample is representative of the fluid volume flowing in the pipe are inaccurate since they rely on assumptions which typically are not encountered since the sample remains, de facto, only a small fraction of diverted fluid. Additionally these measurement systems become more complex because necessary periodic recalibrations are required in the laboratory, to account for the different dielectric constants (E values) which vary with density and chemical composition of the crude oil collected by the tanker en route from different fields. These recalibrations are performed, using the same cumbersome sampling and separation process(es) described above.

In steam injection control, no method seems to be considered reliable for consistent practical application. The techniques available suffer from such shortcomings as lack of representativity and dispersion pattern errors as the ones encountered in water in oil mixtures.

SUMMARY OF INVENTION

It is an object of the present invention to provide an improved method of continuously measuring the dielectric constant (E) and thus overcoming the observed difficulties arising from a heterogeneous mixture of water in oil or in steam. It is a further object of the present invention to recognize the non-homogeneous nature of crude oil or steam deliveries and disclose an invention which does not rely on a gross assumption that the water in oil or in steam mixture is homogeneous and unaffected by temperature.

It is a further object of the present invention to obviate the necessity of time consuming 'recalibrations' which are typically performed in a laboratory to calibrate an instrument under ideal conditions for service in conditions which are less than ideal.

It is a further object of the present invention to disclose an apparatus and method for continuous measurement of water volume in oil or in steam which overcomes many of the shortcomings of the prior art methods which only sampled a small cross section of the volume.

It is a further object of the present invention to apply the present structure for measuring dielectric constant (E) to substances other than water in oil; the latter being a notable example because of its wide range of application and economic importance.

It is a further object of the present invention to overcome the shortcomings encountered in the prior art devices by placing a dielectric capacity probe inside the main pipeline, to measure the average dielectric constant (E) of the flowing mixture. This 'in situ' sampling, will account for the entire cross-sectional area of the pipe or duct and its contents. The 'in situ' probe will have a high intrinsic capacitance approaching that of air, which has a dielectric constant equal to "1". The probe placed within the pipeline shall offer a minimal impedance to flow of the crude oil or steam and the oil's normal impurities and sediments. The probe will automatically self-calibrate, 'in-line', at selected time intervals and shall be fully automated for the overall routine operation. Additionally it is an object of the present invention to continuously correct the measured capacitance as the temperature fluctuates throughout delivery.

One of the unique and novel aspects of the present invention is that the probe is to be mounted inside the main line and substantially fill the entire cross-sectional area.

BRIEF DESCRIPTION OF THE DRAWINGS

FIGS. 1A, 1B, 1C, 1D and 1E illustrate five possible distributions of water in oil which may be encountered in a pipeline in typical off-loading operations.

FIGS. 1AA and 1BB illustrate electrical equivalents of FIGS. 1A and 1B respectively.

FIG. 3A illustrates one method of isolating the positive from the negative plates at the time the capacitor network is installed in a pipeline. FIG. 3AAA also illustrates the type of instrumentation which is required to measure the capacitance within the capacitor network and consequently the dielectric constant of the fluid within the pipeline.

FIG. 3AA is a cross-section of FIG. 3A.

FIG. 3B illustrates the typical location of the capacitor network shown in FIG. 2D in a square or rectangular cross-section of a pipeline.

FIG. 4 illustrates the correlation between the dielectric value and the percent of water for seven crude oils.

FIG. 7-A (and FIG. 7-B, for its equivalent circuit) illustrate the approximate placement of concentric plates in a circular cross-section of the pipeline and an equivalent circuit for the concentric placement of the capacitor plates (in this case, the unequal gaps between plates insure identical volumes between each set of 2 contiguous plates).

DETAILED DESCRIPTION OF THE PREFERRED EMBODIMENTS

One of the objects of the present invention is too overcome many of the problems encountered by prior art methods and apparatus in the measurement of water content in crude oil or in steam. This and other objects of the present invention will be described herein. Although the preferred embodiments relate to specific physical configurations for placement of capacitor electrodes, this invention is not limited to any specific physical geometric configuration.

To overcome some of the short-comings of the prior art devices the present invention overcomes the difficulties arising from heterogeneous sampling of water in oil or steam mixtures. The present invention provides for more accurate results while at the same time minimizing the necessity for time consuming recalibrations which by necessity are performed in the laboratory. Additionally the present invention achieves the goal of providing continuous measurement of water volume in oil or steam over the whole delivered bulk mixture.

It should be noted, that the method and apparatus disclosed herein for measuring the dielectric constant (E) may equally apply to substances other than water in oil or steam, however, the latter are a notable example because of its wide range of application and economic importance.

A unique feature of the proposed invention is that a capacitor array is to be mounted inside the main line in a manner which substantially fills the entire cross-sectional area of the pipeline. This is the equivalent of a large number of very small elementary capacitors, of identical air capacitance. These units are connected electrically, in-parallel, in a symmetrical pattern; wherein, each capacitor contains the same volume of dielectric material between its individual electrodes (or plates).

One of the shortcomings of a concentric arrangement of capacitor plates in a circular cross-sectional area is that the capacitance is unequal for equal distances between plates due to the increasing circumference of the plates. Thus the volume of dielectric material between the plates will vary as a function of the circumference of the plates. This shortcoming can be overcome by reducing the spacing between the plates as the circumference is increased.

Figure 2A:
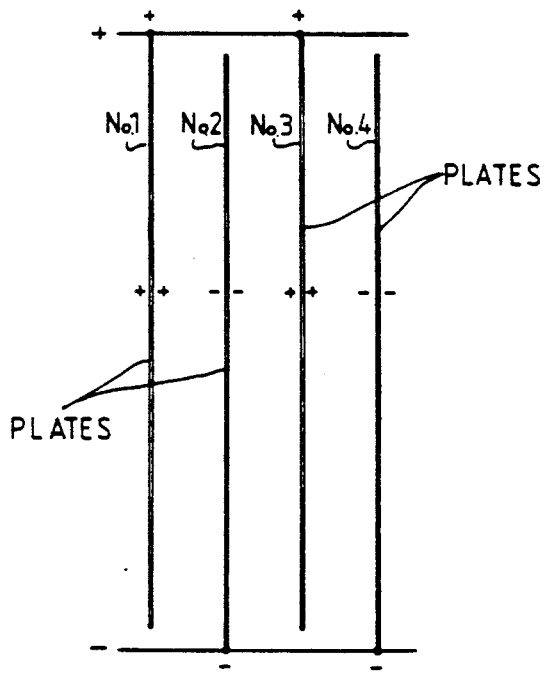
FIG. 2A illustrates one of the preferred embodiments for the present invention depicting long, thin and narrow metal 'plates', each connected 'in-parallel'; and, each having alternatively 'assigned' 'positive' and 'negative' polarities. For the sake of simplicity, only four plates are shown.

To implement the configuration set forth in FIGS. 3A or 3B, it is necessary to use long, thin and narrow metal plates, each connected in-parallel; and, each having alternatively assigned positive and negative polarities, as illustrated in FIG. 2A, (for the sake of simplicity, only four plates are illustrated).

Figure 2B:
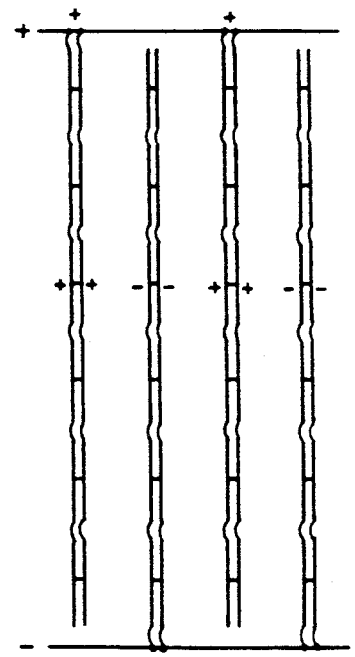
FIG. 2B illustrates an equivalent circuit for the embodiment illustrated in FIG. 2A.

To establish the electrical equivalency of the long, narrow, plates and the large quantity of small capacitors, FIG. 2B is a hypothetical representation of each plate, which is split into a larger number of interconnected smaller plates. In summary, both FIG. 2A and FIG. 2B are electrically equivalent, as is obvious to those of ordinary skill in the art.

Figure 2C:
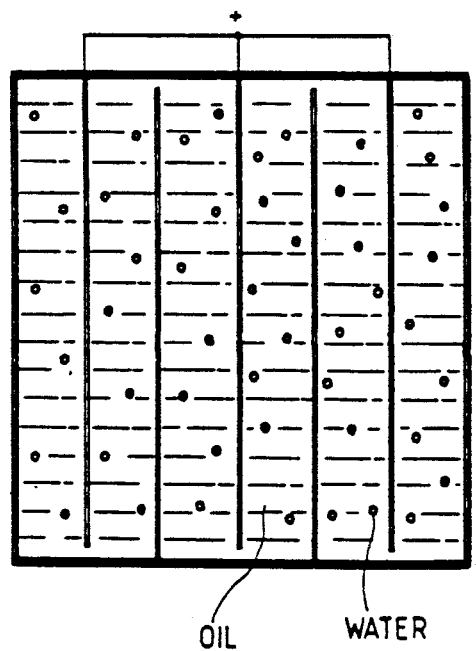
FIG. 2C and 2D illustrates another embodiment of the present invention illustrating the capacitor plates installed in a square or rectangular cross-section of a pipeline, with FIG. 2C illustrating a homogeneous distribution of water in oil and FIG. 2D illustrating a non-homogeneous distribution of water in oil commonly associated with the initial transfer phase or an non-turbulent condition.
Figure 2D:
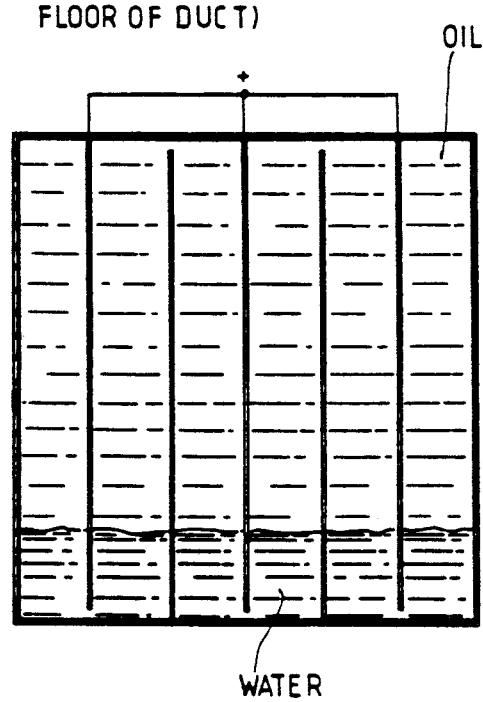

An arrangement of capacitors such as that illustrated in FIGS. 2A, 2B and 2C functions as a sensor to the fluid within the entire pipe cross-sectional area; and, will contain its own dielectric (oil, water or both) because all of the capacitors are identical and connected in-parallel. Additionally the total capacitance of the particular configuration is the sum of the smaller individual capacitances, the total measured capacitance will represent the average of all the smaller capacitances contributing to the measurement.

Expressed mathematically:

C = The intrinsic capacitance of each small (elementary) capacitor.
$E_1$ = The dielectric constant of capacitor #1.
$E_2$ = The dielectric constant of capacitor #2.
$E_3$ = The dielectric constant of capacitor #3.
$E_n$ = The dielectric constant of capacitor #n.
$C_t$ = The capacitance of the number of capacitors connected in electrical parallel.

Thus:

$$C_t = C_{E1} + C_{E2} + C_{E3} + \ldots\ldots C_{En}.$$

$$C_t = C_{(E1+E2+E3+\ldots\ldots En)}.$$

$$C_t = C \times \text{(the average dielectric constant (E) of the fluid mixture of the pipe cross-sectional area)}.$$

If the dielectric fluid in the pipe is water only, $C_t$ is maximum:

$$C_t = C \times n \times E_{water}$$

If the fluid is oil or steam only, then Ct becomes minimum:

$$C_t = C \times n \times E_{oil}$$

$$\text{or } C_t = C \times n \times E_{steam}$$

For mixtures of oil or steam and water, $C_t$ values will be between both maximum and minimum of the above. In summary, $C_t$ will reflect an 'average' of the fractional water volumes of the mixture flowing through a array of plates which cover the entire inside cross-sectional area.

Several arrangements of these small plates connected in-parallel are possible. For simplicity a square or rectangular design will be used to explain the unique aspects of this system for measuring capacitance and consequently water content in oil or steam.

The parallel plates within the capacitor array or network are assembled in a manner which substantially traverses the cross-sectional area of a duct. Preferably the duct is square or rectangular in shape, however other equivalent geometrical configurations are also envisioned. The duct is fitted in a manner such that it is in-line to pumping pipe carrying the fluid to be measured for water content and is held in place with appropriately designed couplings or pipe flanges. Although relative size is not of primary importance, the duct cross-sectional area should be smaller than the pipe, so as to increase fluid velocity, turbulence, mixing and homogeneity.

Another design, which avoids the use of a duct, would be to insert the square array of plates directly into the circular pipe via an elongated narrow window, peripherally sealed and parallel to the pipe's longitudinal axis.

A detailed example of such an assembly is illustrated in FIG. 3A. FIG. 3A depicts one embodiment of the present invention and is not intended to limit the scope of the present invention.

In FIG. 3A, narrow elongated metal plates or rods (or other comparable geometric configurations suitable for use as capacitor plates) [hereafter all collectively referred to as plates] 1 are attached at attachment point 3 by means of welding or some other comparable attachment means which produces a low-conductivity path or short-circuit to insert 2. Each plate or rod 1 and its associated insert 2 is then coated with a layer of hard electric insulating material, such as dielectric tape or enamel or other comparable insulating material. The inserts 2 are then inserted into a narrow, elongated, perforated rectangular cover 4 which is constructed of a hard, non-hydroscopic, non-conductive material, such as fiberglass or polyvinyl chloride (pvc). The design is of very high tolerances, achieving a close of fit between the inserts 2 and the perforation 5 of cover 4. The cover 4, has clamping 'shoulders' 4a (in the illustrated configuration) to allow the unit to be sealed and bolted to the pipeline or fluid duct 13. Each plate or rod 1 is installed in a manner such that the rod or plate 1 is substantially perpendicular to the cover's longitudinal axis (x—x'), see top view. The plates are secured to the cover by close fitting 'locking pins' 6 which are inserted in the conforming counterpart pin holes 6a in insert 2. Inserts 2 are alternately interconnected to conducting bars 7. These conducting bars 7 are arranged in such a manner, that the odd numbered plates 8 are electrically connected together, but electrically isolated from the similarly installed even numbered plates 9. The completely interconnected odd numbered plates 10 become, in effect, the positive electrode (or plate) of a working capacitor. Similarly the interconnected even numbered plates 11 become the negative electrode (or plate) of a working capacitor and are connected by a lug (12) (or any other conventional means) to the body of the pipe, which is at ground (earth) potential and is the 'negative' electrode of the capacitor.

To minimize surface corrosion and galvanic activity between the locking pins 6 and the counterpart pin holes 6a of the inserts 6 and to insure dependable electrical contact between the locking pins 6 and the counterpart pin holes 6a of insert 2 the pins 6 and inserts 2 should be constructed of similar metals.

The completed assembly described above, is to be inserted into a pipe or duct 13 positioned such as to cover the duct's entire cross-sectional area. Although a square or rectangular duct 13 is illustrated this feature is not viewed as a particular limitation of the present invention. The duct 13 consists of a rectangular window 14 which is slightly wider than the cover width "w", (illustrated in the side view of FIG. 3A) of the wall of the duct. The shoulders 4a of cover 4 are secured to the duct's flange 15 with a series of bolts, nuts and washers 16, which are conventional in design within the piping industry. A flat rubber washer 17 is positioned between the cover's shoulders 4a and flange 15, to insure a reliable seal between the two machined metal surfaces.

The opposite end of each plate or rod 18 is attached to a thin, flat, hard, rectangular insulating strip 19 which is constructed of the same material as that used for the cover 4. Inserting the plate or rod ends 18 with narrow, parallel grooves 21, machined into the strip's face, will enhance the adhesion of the plate ends 18 to the strip 19. An non-conductive adhesive 20 is used to adhere plate ends 18 to strip 19. Further uses of the word adhesive will refer to any material, i.e. epoxy resin, that has the properties of a chemical fastener or substance that can, by application, render an object impermeable to gases and/or fluids).

A flat, thin sheet of soft rubber 22, dimensionally identical to strip 19 is joined to the reverse face of the strip, using an adhesive. The rubber 22 functions as a seal between the strip 19 and duct wall, and also increases the mechanical resiliency of the strip 19.

With the plate spacings between plates substantially equal and substantially identical spacings existing between the outboard plates 23 and 24 and the duct's wall 13, then the capacitor and its specific array, may be considered complete in construction.

The ends 25 of the insert 2 are coated with an adhesive 26 which seals the assembly against fluid leakage from the inside and through the interface 27 between the inserts 2 and the perforated walls 5 of cover 4. Under normal conditions, the pressure differential between the inside of the pipe and atmosphere is quite low; therefore, this simple method of sealing should be sufficient against leakage. Should conditions of a high pressure differential be encountered, the design can be easily modified by using conventional O-ring seals (28) as well as other sealing methods well known in the art.

The configuration illustrated intentionally limits the occurrence of stray (i.e. 'inter-rod') capacitances, by minimizing areas and maximizing gap widths. The effect of the enamel coat on the plates is minimal because of its thin coating applied and the fact that the enamel is electrically equivalent to a high stray capacitance, connected in series, to the measured capacitance and considering that the reciprocals of capacitances add in the series connected mode.

In design and function, the capacitor has two important variables. These are:
1) The width of the plates 1 designated as "$w_p$".
2) The gap between the plates "g".

The wider the '$w_p$', and the narrower the 'g', the greater, becomes, the overall capacitance of the array of plates. This results in a larger number of small equivalent capacitances and better resolution of the measured signal.

One of the inherent shortcomings of the above-described configuration is the development of a proportionally greater in-line resistance to fluid flow. Therefore, a balance must be attained between '$w_p$' and 'g' to achieve optimal electrical and mechanical results. A practical example will demonstrate how such calculations can be formulated:

The example assumes that a housing with a total cross-section of three square feet, one inch wide "$w_p$" plates separated by a one-half inch gap (g), would provide an intrinsic capacitance of approximately 400 picofarads. This minimal capacitance insures a quantitative and qualitative resolution of measurement of signals above electrical 'noise' levels, with minimum resistance to 'in-line' fluid flow.

With this unique design, several options are available for monitoring changes in fluid capacitance flowing through duct 13. Commercially, Hewlett-Packard (H-P) manufactures several highly sensitive and accurate instruments which can be integrated into the system. For example an H-P model 4278-A would be an acceptable capacitance meter to measure the capacitance encountered by parallel plates within duct 13.

Another comparable means of measuring the capacitance of the plates would be to arrange the electrical circuitry such that one of the elements can function as a precise bridge 29. The bridge input may be powered by an oscillator (30) such as an H-P Model 3314-A, which is noted for its versatility, accuracy and dependability. The bridge output is a frequency signal (f) which is directly proportional to the square root of the capacitance (C) of the described array and can be calculated as follows:

$$f = k/C^{\frac{1}{2}} \quad (1)$$

where k is a constant derived from components of the bridge.

To determine the frequency of the measurement a high resolution frequency counter 31, such as an H-P Model 5314-A is connected at the output of the bridge. This instrument may be used to send the varying measured frequencies to a computer terminal 32 which may be used to convert the measured electrical signals directly into values of fractional water volumes. The latter would be electronically displayed on a display 33 after appropriate processing and conditioning of the signal to permit display on such displays as seven segment display, light emitting diodes, fluorescent tubes or liquid crystal cells.

In the alternative the dielectric constant can also be determined by measuring the phase shift of the frequency in lieu of determining the absolute frequency by means of a counter or other method.

The computer 32 includes a water totalizer, which integrates (over time) the instantaneous fluctuations in water volume. This integrated (or totalized) value may the be recorded on a commercial strip chart recorder 34, such as H-P Model 7090-A ("Plotter-Recorder"). All measured data may be stored on common disks or tape.

Due to minute variations in tolerances between units, each capacitor array requires calibration in the laboratory. This initial calibration is conducted in dry air, which has a minimum dielectric constant (E) of 1. Should other dielectric material fill the inter-plate gap, the capacitance of the array will increase. A maximum value of E is attained when the substance is 100% water.

It is recognized by the petroleum industry, that the range of interest in ratio of water to oil (W/O+W), in the practical deliveries of crude oil is 0.0% to 1.0% whereas for water in steam this range is 0.5 to 3%. Precisely conducted tests of E on various oil and water mixtures (all well homogenized, and of various geographic origins) have been published by British Petroleum (BP). These results are described by the curve shown in FIG. 4. Illustrated in FIG. 4 are the variations of water volumes in percent (%) versus the average crude's dielectric constant (E), in the range of zero to 50%. It is important to note that this curve is linear in the lower range, i.e. 0% to 5%.

Independently and without reference to the study by BP, the applicant's invention arrives at the same conclusions and establishes numerical agreement with the data published by BP. The applicant uses an algorithm which was derived from a mathematical model published in 1914 by K-W Wagner, (Arch. Elektrotech. 2, 378). This model, called the Maxwell-Wagner Model, evaluates the dielectric constant (E) of a suspension of electrically conductive particles of small diameters in a non-conductive dielectric medium. The Maxwell-Wagner model corresponds exactly to the oil and water or steam and water mixtures encountered in practice.

As the Maxwell-Wagner model requires, it is first legitimate to model the mixture as spherical droplets of water dispersed in a continuous phase of oil or steam. Text books of physics state that a immersed liquid assumes, under its surface tension, a shape that offers the minimum area to the surrounding fluid; this shape is a sphere.

The Maxwell-Wagner equations imply that neither the size of the water particles, nor the magnitude of their electric conductance (or salinity) and dielectric constant (E), or their dispersion patters have any bearing on the bulk dielectric constant (E) of the mixture in the low water volume range. These physical facts are confirmed by the publications of BP.

Besides, the Maxwell-Wagner model assumes, as a primary condition for its validity, that the electric field to which the mixture is submitted, is constant. This condition fits perfectly the parallel plate capacitor since this field is constant according to the electrostatic theory. It also fits, but not perfectly, the cylindrical capacitor designed by Endress-Hauser under BP sponsorship, since the inter-electrode gap is so thin that the electric field therein is almost constant (in cylindrical capacitors, the inter-electrode field varies as the inverse of the distance from the inner electrode, small gaps between electrodes means almost constant distance from the inner electrode therein.)

Under a constant electric field, it can be demonstrated that the global dielectric constant of the inter-electrode mixture is independent of the geometry of the spatial distribution (dispersion pattern) of the water droplets dispersed in the continuous phase, that is oil or steam.

To achieve this independence of mixture dielectric constant from dispersion patterns, Maxwell-Wagner state that the distance between spheres must be large compared to their radii. This applicant has calculated that this condition is fulfilled at water fractional volumes of 5% or less. This figure is compatible with the range of small volumes of water to be evaluated either in oil or in steam. The Maxwell-Wagner model is therefore legitimate.

In the range of zero to 5% of water volume in an oil-water mixture, the linear relation between the fractional water volume (V) and the mixture's dielectric constant (E) is expressed by the following equation:

$$V = \tfrac{1}{3} \times (E/E_{oil} - 1) \qquad (2)$$

where $E_{oil}$ is the dielectric constant of the crude oil being measured

Alternatively $E_{steam}$ should be substituted to $E_{oil}$ in steam water mixtures.

Combining equations (1) and (2), the calculation to be performed by the computer 32 can be expressed as follows:

$$V = (K/E_{oil} \times f^2) - \tfrac{1}{3} \qquad (3)$$

where K is a constant equal to $k^2/(3 \times$ air capacity of the array)

The dependence of 'V' on '$E_{oil}$' is obvious from equation 2). '$E_{oil}$' varies with crude density, chemical composition and temperature. This latter fact, creates the necessity for constant monitoring and measuring the $E_{oil}$, and reveals the wide range of application of the present invention in the petroleum industry.

On the other hand, the dielectric constant of steam if always "1" (one) and independent of temperature and pressure, under the conditions associated with steam injection operations.

Figure 5:
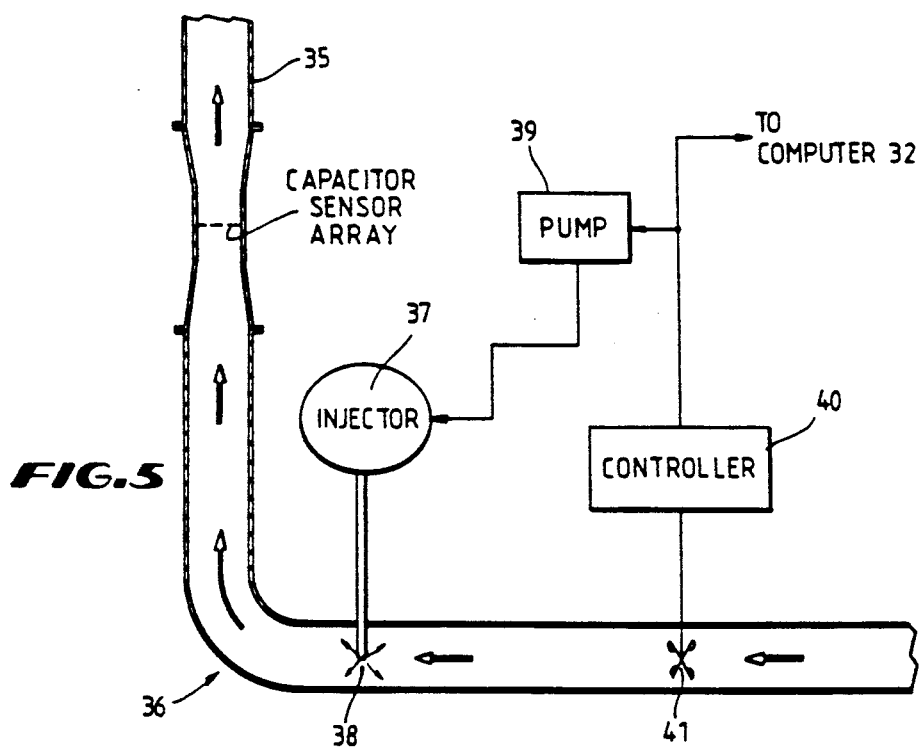
FIG. 5 illustrates an innovative method of calibration which requires the injection of a known quantity water into the crude.

To minimize the need to calibrate the system by employing prior-art sampling and remeasurement of the flowing crude, an innovative method of recalibration is disclosed and illustrated in FIG. 5. For steam-water systems this calibration method is not necessary as $E_{steam} = 1$ for steam injection operations. This method is not viewed as necessary to practice the present invention as only an initial dry (in-air) calibration is necessary to satisfactorily operate the array. However in steady-state flow conditions when a transient may be necessary to satisfy operating personnel that the system is working properly the following calibration procedure is recommended.

In the preferred embodiment the capacitor array is located in a horizontal section of the crude oil pipeline for measuring the water content during the initial transfer phase, and another capacitor array is located in a vertical section of the crude oil pipeline for measuring the water content during the stable transfer phase. In the alternative one capacitor array may be used in either a vertical or horizontal portion of the pipeline, however the use of only one capacitor array would yield accurate results during only one phase of the transfer, e.g. a horizontal array would yield accurate results during the initial transfer phase and a vertical array would yield accurate results in the stable transfer phase. A combination of both a vertical and horizontal array permits one to optimize the system to obtain accurate results throughout the complete transfer of crude from the tanker to the on-shore storage facilities.

For the array located in the horizontal section of the crude oil pipeline it is advisable to locate the array a few pipe diameters downstream of the transition of a circular pipe or duct to a rectangular pipe or duct. Additionally the transition from a circular pipe or duct to a rectangular pipe or duct should be designed in a manner to minimize turbulence and stabilize the oil-water interface level by enhancing segregation.

This horizontal mode configuration takes advantage of the natural segregation of the water at the bottom of the duct under the gravity force field.

In crude oil applications, the algorithm for solving for "V" under this horizontal mode operation is different from the one applicable to low water fractional volumes described by equation 2,). Equation 2 should rather be used as follows:

$$V = (1/(E_w/E_{oil} - 1)) \times ((E/E_{oil} - 1)) \qquad (2')$$

In crude oil applications, $E_w$ is the dielectric constant of the flowing water, which is no longer negligible as in Equation 2, as water is present in very large quantity, compared to oil. If $V = 1$, the measured E is equal to $E_w$.

As the water content of the oil/water mixture decreases, it would be advisable to install, as show in FIG. 3, two parallel plate (single element) capacitors, one at the floor of the crude oil duct to monitor the dielectric constant of the water, one at the ceiling of the crude oil duct, to monitor the dielectric constant of the oil, both fluids being, as we know, segregated by gravity forces, under conditions of horizontal flows. These two fundamental data points will be available for the processing of the second phase.

For the array located in vertical section, it is advisable to locate the capacitor array in a vertical section of pipe 35, preferably downstream from an elbow or bend 36, where greater turbulence improves the homogeneity of the crude/water mixture.

Referring now to FIG. 5 and specifically applicable for calibration purposes, in crude oil applications, upstream from 36 a water injector 37 is inserted inside the pipe, with its injector head 38 located at the centerline of the pipe. A pump 39 injects water intermittently during selected time intervals. The pump action is directed by a typical industrial controller 40. The input signal to the controller 40 comes from a flowmeter 41 which sends an electrical signal directly proportional to the rate of flow inside the pipe. The controller output instructions direct the pump to inject water into the crude flow, a fractional volume ($V_o$) of water. Under such conditions, the frequency output from the counter 31 changes from value 'f' to a new value '$f_o$' and equation (3) can be rewritten as:

$$V + V_o = (K/(E_{oil} \times f_o^2)) - \tfrac{1}{3} \qquad (4)$$

Eliminating 'V' from equations (3) and (4) yields:

$$E_{oil} = (K/v_o) \times (1/f_o^2 - 1/f^2)$$

The computer 32 performs the necessary calculations and based on the foregoing equations and enters the new calculated value of $E_{oil}$ into equation (3).

The water injection rate, duration and quantity are determined by local conditions. For example, if the type of crude oil and its temperature are expected to be relatively stable, limited control only, may be required, (in such cases, it may even be performed manually). Note that the newly derived value of $E_{oil}$ is automatically corrected for temperature; thus, obviating the need for temperature control. In some installations, water injectors are already installed for periodical calibration checks.

It is advisable to monitor the entire discharge operation (from the ship to the storage tanks) beginning with the first phase; wherein, appreciably more water than oil is drawn into the 'inlet pipe'. Subsequently, a more accurate and efficient evaluation of the water to oil ratio (W/O+W) of the bulk of the cargo is achieved. The curves described in FIG. 6 (which were extrapolated from those in FIG. 4), compare the range of fluid capacitance in values during the 'first' and 'second' phase of the discharge process. Note that if the range of interest in water volume evaluation is set to a maximum of 1%, this would correspond to an approximate dielectric constant (E) in the narrow range of 2 to 2.4. In the high water volume range, the dielectric constant (E) of the fluid is highly dependent on the salinity of the water. It is, therefore, advantageous to begin early monitoring of dielectric constant (E) during initial discharging of the crude oil, so that an accurate evaluation of the gross amount of water can be determined, before the critical 1% fractional water volume is attained. Thereafter, the precise measurement of water volumes in the second phase would be determined by computer program as previously described.

Figure 6:
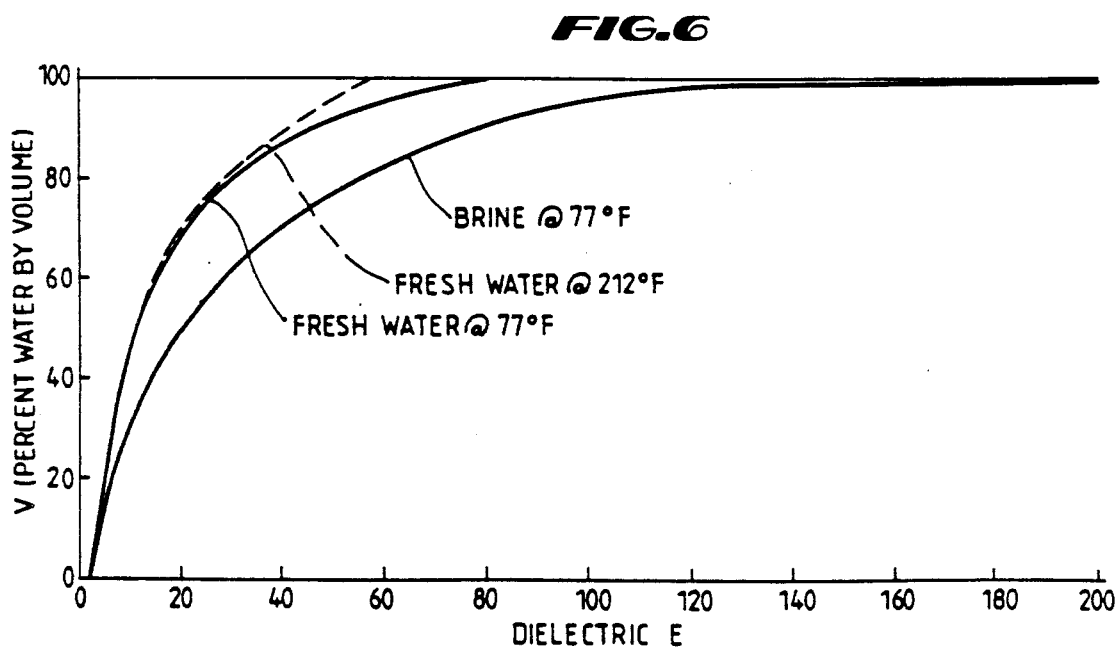
FIG. 6 illustrates some of the values which were extrapolated from FIG. 4) to compare the range of the fluid capacitance values during the 'first' and 'second' phase of the discharge process.

In the event that a single mode vertical operation is desired, implementation of a calibration curve such as the ones shown in FIG. 6 in the high water content range, is necessary. Initial values of dielectric constants of the water and oil involved in the flow, must be known, since the calibration curve is dependent upon temperature and water salinity. These values are obtained from laboratory analysis of in-line collected samples or in the alternative by the single element capacitors installed at the top (for oil dielectric) and the bottom (for the water dielectric) of the material contained in the pipeline upstream of the capacitor array.

Since the calibration curve is non-linear; conventional methods of numerical analysis should be used in order to program the computer in an appropriate manner. Straight or curved segments approximation equations are two of such methods. The computer program outputs the value "V" of the function, from the processing of the input variable "E".

Continuous temperature monitoring is recommended and subsequent fluid resamplings may be necessary, until the injection process for automated recalibration is initiated.

Errors due to non-homogeneous fluids should be expected; for this reason, the horizontal mode of operation during the first phase of crude unloading is recommended, not only on account of its accuracy, but also on account of the relative simplicity and efficiency of the method used in handling the data.

The procedure continues, until the 1% water volume is detected; thereafter, the computer is then programmed to obtain:
1) Accurate water in oil evaluations and to
2) Periodically inject water for recalibrations of the capacitor array.

Prior to reaching the 1% detection level, a sample of crude is collected through the same shunt as the water sample, mentioned above for the prior art devices. The water is removed from the sample in the laboratory, and its $E_{oil}$ value is measured in a conventional cell. After this initial $E_{oil}$ is entered manually into the computer program, the automated monitoring process can begin. Estimates are that a capacitor bridge design operating at a frequency of 100 kilohertz would maintain a sensitivity of about 14 hertz for every incremental water volume in oil of 0.01%.

The whole process would be enhanced by the use of static mixers, mounted in-line and upstream from the monitoring instrumentation. Komax, manufactures such a mixer which requires no external power to operate, however such mixer introduce a minor pressure drop due to the restriction imposed on the flow. With a mixer such as that suggested turbulence and the concomitant homogenization of the crude are created by the geometrical configuration of the mixing elements themselves.

Between oil deliveries or steam injection operations, the capacitor array can be removed from the line, cleaned and recalibrated in 'dry air'. A dry air, condition can be achieved by using a blow torch or other heating device. The bridge and associated electronics can be checked against a fixed capacitor of known value.

As previously mentioned, a rectangular or square duct housing an array of parallel plates is but one of several possible electrode configurations which will satisfy the requirements for obtaining identical capacitances and measuring dielectric volumes. However, other configurations may be selected to practice the present invention.

The embodiment show in FIGS. 7A and 7B is attractive in that cylindrical capacitors conform to pipeline cross-sections which are circular, however, when concentric cylindrical capacitor plates are used, it is virtually impossible to achieve equality of elementary volumes and capacitances as in the case of parallel plates; one suffers at the expense of the other. Under such conditions, design simplicity and minimal encumbrance are achieved at the cost of measurement accuracy.

Even though identities of capacitances and dielectric volumes may be achieved for all capacitors, unlike the parallel plates pattern in a rectangular duct the shapes of the capacitors cannot be superimposed since each capacitor's gap decreases as the pipe radius increases (with corresponding increases in circumferential lengths). Therefore, the uniformity of distribution of elementary capacitors is not as good (in a circular cross-section) as the design with parallel plates in a rectangular cross-section.

This particular concept of uniformly spread, small, identical capacitors is applicable, not only to whole inner cross-sectional areas of pipes but also to 'bypass loops', as previously described. A small area configuration can be set at the center line of the pipe, or for that matter, anywhere within this cross-sectional area, if a particular spot of the inner cross sectional area is to be tested.

The present invention is not limited to pipelines at tanker terminals. The need for such monitoring or measurement may be required in inland pipelines, refinery piping, and other similar applications. The apparatus may also find use in the laboratory as well.

This innovative calibration method disclosed herein, eliminates the need for physical separation of water from oil (the latter, is known to be lengthy and cumbersome), and is applicable to laboratory or factory calibration. Its reliability can be further improved by conducting multiple injections at various water volume rates, in order to provide several equations for solving, more accurately, the unknown variable $E_{oil}$, which is measured by the more conventional methods.

The present invention applies not only to liquids, but to an substance and in any phase. An example of a liquid-gaseous mixture (which, is of prime interest to the oil industry) is the steam injected into oil wells for enhanced recovery of heavy oils. It is important that the water content in the mixture be kept at an optimum value. Since the dielectric constant of steam is exactly '1', the contrast with the values of dielectric constants of various waters, provides an incentive, by industry, to utilize the method described herein. Additionally this method can be utilized to design steam quality probes either in surface measurements or in downhole measurements, the latter, being commonly referred to as 'well logging'.

What I claim is:

1. An improved apparatus for detecting and calculating bulk water content in steam comprising:
   a) a capacitor array, said array conforming to the cross-section of a duct used to transfer the steam, said capacitor array inserted in the steam duct;
   b) a capacitance measurement system;
   c) a means to calculate the water content of the steam conveyed in said duct based on the measured capacitance.

2. The apparatus described in claim 1 wherein the duct used to transfer the steam is formed with walls which are substantially at right angles to each other and the capacitor array is a set of parallel plates within said duct, said plates forming a plane which is substantially at right angles to the longitudinal axis of said duct.

3. The apparatus described in claim 2, wherein the set of parallel plates occupies substantially the entire cross-sectional area of the duct.

4. The apparatus described in claim 1, wherein the duct used to transfer the steam has a substantially circular cross-section and the capacitor array is a set of concentric plates within said circular duct.

5. The apparatus described in claim 4, wherein the set of concentric plates occupies substantially the entire cross-sectional area of the circular duct.

6. The apparatus described in claim 1 wherein said duct is positioned in the horizontal plane and further comprises at least one single element capacitor inserted upstream of said capacitor array and positioned at the bottom of the duct.

7. The apparatus described in claim 6, wherein a second capacitor is used to measure the dielectric constant of the water.

8. The apparatus described in claim 7 wherein a third capacitor is used to measure the dielectric constant of the steam.

9. The apparatus described in claim 1 further comprising a temperature measurement system wherein the measured capacitance is compensated based on the measured temperature of the steam.

10. An improved apparatus for detecting and calculating bulk water in steam comprising:
    a) a plurality of parallel plate capacitors for monitoring the electrical capacitance of steam in a duct used to transport said steam, said capacitors conforming to the cross-section of said duct;
    b) a capacitance measurement system;
    c) a means to calculate the water content of water in the steam based on the measured capacitance.

11. The apparatus described in claim 10 wherein the steam is placed in a duct formed with sides which are at substantially right angles and plurality of capacitors is a set of parallel plates which form a plane which is substantially at right angles to the longitudinal axis of the duct.

12. The apparatus described in claim 11, wherein the set of parallel plates occupies substantially the entire cross-sectional area of the duct.

13. The apparatus described in claim 10, wherein the steam is placed in a duct which has a substantially circular cross-section and the plurality of capacitors is a set of concentric plates within said circular duct.

14. The apparatus described in claim 13, wherein the set of concentric plates occupies substantially the entire cross-sectional area of the circular duct.

15. The apparatus described in claim 10 wherein said duct is positioned in the horizontal plane, further comprising a second capacitor, said second capacitor inserted upstream of said capacitor array and positioned at the bottom of the duct.

16. The apparatus described in claim 15 further comprising a third capacitor, said third capacitor inserted upstream of said capacitor array and used to measure the dielectric constant of the steam.

17. The apparatus described in claim 15 wherein said second capacitor is used to measure the water content during the initial transfer phase.

18. The apparatus described in claim 10 further comprising a temperature measurement system wherein the measured capacitance is compensated based on the measured temperature of the steam.

19. An improved method of measuring and calculating bulk water in steam comprising:
    a) inserting a capacitor array in a duct used to convey steam, said array substantially conforming to the cross-section of said duct;
    b) measuring the capacitance of the steam conveyed in the duct;
    c) calculating the water content of the steam conveyed in said duct based on the measured capacitance.

20. The method described in claim 19 wherein the bulk water is continuously measured and calculated.

21. The method described in claim 19 further comprising measuring the temperature of the steam conveyed in the duct.

22. The method described in claim 21 further comprising compensating the capacitance based on the measured temperature.

* * * * *